United States Patent
Kumar et al.

(10) Patent No.: US 10,889,549 B2
(45) Date of Patent: Jan. 12, 2021

(54) CONTINUOUS PROCESS FOR THE PREPARATION OF 2-(1H-IMIDAZOL-4-YL) ETHANAMINE AND PHARMACEUTICALLY ACCEPTABLE SALTS THEREOF

(71) Applicant: Jubilant Generics Limited, Noida (IN)

(72) Inventors: Sanjeev Kumar, Noida (IN); Rajesh Kumar, Noida (IN); Brijesh Kumar Shukla, Noida (IN); Rajendra Singh Shekhawat, Noida (IN); Sujay Biswas, Noida (IN); Dharam Vir, Noida (IN); Nirmal Kumar, Noida (IN); Indranil Nandi, Yardley, PA (US)

(73) Assignee: Jubilant Generics Limited

( * ) Notice: Subject to any disclaimer, the term of this patent is extended or adjusted under 35 U.S.C. 154(b) by 0 days.

(21) Appl. No.: 16/732,626

(22) Filed: Jan. 2, 2020

(65) Prior Publication Data

US 2020/0131137 A1     Apr. 30, 2020

Related U.S. Application Data

(63) Continuation-in-part of application No. PCT/IB2017/050610, filed on Dec. 22, 2017.

(30) Foreign Application Priority Data

Jul. 3, 2017  (IN) .............................. 201711023282

(51) Int. Cl.
*C07D 233/64*    (2006.01)
*B01J 31/02*     (2006.01)

(52) U.S. Cl.
CPC ........ *C07D 233/64* (2013.01); *B01J 31/0208* (2013.01); *B01J 31/0209* (2013.01); *B01J 31/0232* (2013.01); *B01J 31/0248* (2013.01)

(58) Field of Classification Search
CPC .................................................. C07D 233/64
See application file for complete search history.

(56) References Cited

U.S. PATENT DOCUMENTS 6,403,806 B1   6/2002   Yeh et al.
7,485,756 B2   2/2009   Omeis et al.

*Primary Examiner* — Shawquia Jackson
(74) *Attorney, Agent, or Firm* — William D. Hare, Esq; McNeely, Hare & War, LLP

(57) ABSTRACT

The invention relates to a commercially viable, cost effective and energy efficient process for the preparation of 2-(1H-Imidazol-4-yl)ethanamine or pharmaceutically acceptable salts thereof in high purity and yield via application of continuous flow technology.

20 Claims, No Drawings

CONTINUOUS PROCESS FOR THE PREPARATION OF 2-(1H-IMIDAZOL-4-YL) ETHANAMINE AND PHARMACEUTICALLY ACCEPTABLE SALTS THEREOF

CROSS-REFERENCE TO RELATED APPLICATIONS

This application is a continuation-in-part of PCT/IN2017/050610 filed on Dec. 22, 2017.

FIELD OF THE INVENTION

The present invention discloses a commercially viable, cost effective and energy efficient process for the preparation of 2-(1H-Imidazol-4-yl) ethanamine or pharmaceutically acceptable salts thereof in high purity and yield via application of continuous flow technology.

BACKGROUND OF THE INVENTION 2-(1H-Imidazol-4-yl)ethanamine (histamine), represented as the compound of formula I, possesses significant biological activity and is used as a standard in biological assays and as a component in certain allergy diagnostic kits. Histamine occurs widely in nature, but to take full advantage of its therapeutic properties, it is important to obtain large quantities of histamine of pharmaceutical grade by synthetic routes.

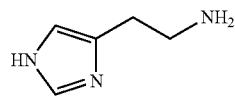

I

Histamine in therapeutic applications is used as its dihydrochloride salt, which can be conveniently synthesized by decarboxylation of histidine. Using this synthetic process, histidine is decarboxylated and subsequently treated to form the dihydrochloride salt form of the molecule.

Hashimoto et al. in *Chemistry Letters,* 1986, pages 883-896, discusses the preparation of histamine, wherein histidine is decarboxylated using cyclohexanone as a catalyst in cyclohexanol solvent. The process disclosed involves the decarboxylation reaction being carried out in 26 hours, and used toluene and HCl gas for the preparation of the dihydrochloride salt. The process disclosed is not industrially feasible as the reaction time is too long, which results in a lot of energy consumption, and further the process fails to provide histamine dihydrochloride of pharmaceutical grade as it contains a number of impurities which makes the process unsuitable for large scale production.

JPH05255204 discloses use of acetophenone catalyst and diethylene glycol as a solvent for the decarboxylation of histidine to histamine. The said process is also reported to be inconsistent in providing histamine dihydrochloride in desired purity and yield. Further, the process disclosed suffered the incompatibility in terms of removal of traces of diethylene glycol as histamine and its dihydrochloride salt are highly soluble in water and none of the isolation techniques worked efficiently to remove the diethylene glycol solvent from the product. Thus, owing to various disadvantages of the disclosed process, it is rendered inapplicable at an industrial scale.

Thus, there exists a need in the art for the development of an industrially feasible, cost effective, economic and simple process capable of controlling the impurities, for producing histamine or pharmaceutically acceptable salts thereof with high purity and high yield.

Accordingly, as an alternative to the prior art methods, in the present invention improved conditions have been optimized for the synthesis of histamine or pharmaceutically acceptable salts thereof by application of continuous flow reactor technology. Compared to traditional methods and processes, the present process can have or has distinct advantages in regard to cycle time, energy consumption, and product purity.

OBJECT AND SUMMARY OF THE INVENTION

The principal object of the present invention is to provide an improved and efficient process for the preparation of histamine or pharmaceutically acceptable salts thereof which is simple, economic and alleviates one or more problems of the prior art disclosed processes.

It is another object of the present invention to provide a cost effective and industrially feasible process for producing histamine or pharmaceutically acceptable salts thereof, wherein the process provides high yield and high purity of the desired product by reducing the formation of impurities, in a consistent and reproducible manner.

In accordance with an object, the present invention provides a process for the preparation of histamine or pharmaceutically acceptable salts thereof, comprising
 (a) preparing a solution of L-histidine of Formula II and a catalyst in a solvent;

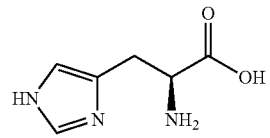

II (b) performing the decarboxylation reaction by feeding the solution of step (a) to a continuous reactor to obtain histamine,
 and optionally converting the histamine to its pharmaceutically acceptable salts.

DESCRIPTION OF THE INVENTION

While this specification concludes with claims particularly pointing out and distinctly claiming that which is regarded as the invention, it is anticipated that the invention, and various aspects of the invention, can be more readily understood through reading the following detailed description of the invention and study of the included examples.

Chemical reactors are vessels, wherein chemical reactions are carried out; their performance determines the reliability and suitability of a process, its environment safety, the consumption of energy and the raw materials required. A continuous reactor is a reactor where there are no moving parts other than pumps that deliver the reactants. To achieve efficient mixing of reactants the addition of static mixing elements such as glass beads inside the reactor is done that provides ideal conditions of radial mixing and continuous flow necessary to perform reactions. One such example of a continuous reactor is plug flow reactor. In a plug flow reactor, the flow of reactants pumped in the reactor is laminar and the properties of the reaction medium, i.e., pressure, temperature, reactant and product concentrations, are the same throughout the entire cross section of flow. Further, all the elemental volumes of the reaction medium remain in the reactor for the same period of time, and the change in concentration, temperature, and pressure with time are identical for each elemental volume. Since, the flow of reactants pumped in the reactor is laminar, and reactant and product concentrations should remain the same throughout the entire cross section of the flow, to maintain equal distribution of concentration of reactant throughout the reactor, the particle size distribution of reactant also plays an important part in achieving the desired results from a continuous reactor. Plug flow reactors usually operate in adiabatic and non-isothermal conditions. Consequently, from the standpoint of kinetic parameters of a chemical reaction under isothermal conditions, plug flow reactors are more efficient than stirred tank reactors.

The present invention provides an improved method for the preparation of histamine or pharmaceutically acceptable salts thereof using a continuous reactor. The process has distinct advantages in regard to cycle time, energy consumption, and yield and product purity over traditional methods. The process employs application of continuous reactor technology for the preparation of desired product in high yield and high purity with enhanced in-process control on impurities with shorter reaction time.

The present invention provides a process for the preparation of histamine or pharmaceutically acceptable salts thereof, comprising (a) preparing a solution of L-histidine of Formula II and a catalyst in a solvent;

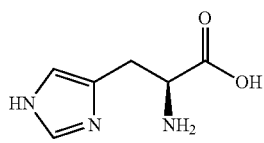

II (b) performing the decarboxylation reaction by feeding the solution of step (a) to a continuous reactor to obtain histamine;
and optionally converting the histamine to its pharmaceutically acceptable salts.

According to the present invention, a solution of L-histidine is prepared using a solvent and a catalyst, wherein a solution can be heterogeneous and homogeneous in nature. The solvent used is selected from the group comprising of alcohols such as methanol, ethanol, propanol, butanol, ethylene glycol and the like; aromatic hydrocarbon such as toluene, xylene and the like, ethers such as diisopropyl ether, t-butyl methyl ether, tetrahydrofuran, dioxane and the like; esters such as ethyl acetate, methyl acetate and the like, halogenated hydrocarbons such as dichloromethane, chloroform, dichloroethane and the like; ketones such as acetone, methyl ethyl ketone, ethyl isobutyl ketone and the like; nitriles such as acetonitrile, propionitrile and the like; aprotic polar solvents such as N-methyl pyrrolidone, N,N-dimethylformamide, dimethylsulphoxide and the like; water or mixtures thereof. The catalyst used is selected from the group comprising of acetophenone, 4-methylacetophenone, 4-nitroacetophenone, 4-bromoacetophenone, benzoyl peroxide, 2,2'-azobisisobutyronitrile, cyclohexanone and the like. The solution of L-histidine and the catalyst is prepared at room temperature. The catalyst is used in 0.5 to 1.5 mole equivalents of L-histidine.

According to one aspect of the present invention, depending upon the particle size distribution of L-histidine, reduction of particle size of L-histidine is carried out before its use, wherein the particle size distribution of L-histidine is reduced to a $d_{90}$ less than 300µ, preferably less than 200µ, more preferably less than 100µ, most preferably less than 50µ. The reduction of particle size distribution is done using processes known in the art such as milling, micronization, jet milling, cryomilling, etc.

According to one aspect of the present invention, the decarboxylation reaction of L-histidine is carried out by feeding the solution prepared in step (a) at the flow rate of 20-200 ml/min at reflux temperature to a continuous reactor. The continuous reactor used is selected from the group comprising of microreactor, plug flow reactor such as coil reactor, tube reactor, and the like. The reaction is optionally carried out under inert atmosphere or under an inert gas stream at reflux temperature of the solvent of the solution. Examples of the inert gas include nitrogen, helium, neon, argon and the like.

The residence time necessary in the method according to the invention, depends on various parameters, such as, for example, the temperature or reactivity of the starting materials. The term "residence time" refers to the internal volume of the reaction zone within the continuous reactor occupied by the reactant fluid flowing through the space, at the temperature and pressure being used. The residence time is between about 30 seconds and about 10 minutes.

After the reaction is complete, the resulting reaction mixture is subjected to various isolation techniques to isolate histamine, such as extraction, filtration, distillation, etc.

According to the present invention, the histamine obtained is optionally converted to its pharmaceutically acceptable salts, with the salt selected from the group comprising of hydrochloride, hydrobromide, tartrate, oxalate and the like. The final product is optionally purified by a suitable recrystallization procedure known in the literature.

According to present invention, the histamine hydrochloride obtained is having a purity not less than 99.9%.

The major advantages realized in the present invention as compared to prior art batch processes are high yield, high purity, consistency, absence or least formation of impurities. These distinctively identified advantages of the reactions in continuous reactor results from minimized residency time and continuous flow nature of the reaction, which thereby reduces the contact time between desired product and unreacted starting materials.

Having described the invention with reference to certain preferred embodiments, other embodiments will become apparent to one skilled in the art from consideration of the specification. The invention is further defined by reference to the following examples describing in detail the preparation of histamine. It will be apparent to those skilled in the art that many modifications, both to materials and methods, may be practiced without departing from the scope of the invention.

EXAMPLES

Example 1: Preparation of Histamine Dihydrochloride

To a solution of L-histidine (100 g) in N-methyl pyrrolidone (950 ml), added acetophenone (58.7 g) at room temperature under nitrogen. The reaction mixture was stirred for about 30 minutes at room temperature under nitrogen. The temperature of circulating oil on plug flow reactor was set to 200-210° C. The plug flow feeding point was fed with the solution prepared above at a flow rate of 40 ml/min at 200-210° C. under nitrogen. The resulting reaction mass from the plug flow reactor was taken into another vessel at 20-30° C. and filtered. To the filtrate, added dichloromethane (50 ml) and slowly adjusted the pH of the reaction mixture to 1-2 using an isopropanol-HCl solution. The resulting reaction mixture was stirred for about 2-4 hours for complete precipitation. The solid obtained was filtered and dried to obtain histamine dihydrochloride.

Yield: 80%

Example 2: Preparation of Histamine Dihydrochloride

L-histidine is milled to reduce particle size distribution of $d_{90}$ of about less than 200μ. To a solution of milled L-histidine (1.4 kg) in N-methyl pyrrolidone (14.0 liter), added acetophenone (0.85 kg) at room temperature under nitrogen. The reaction mixture was stirred for about 30 minutes at room temperature under nitrogen. The temperature of circulating oil on plug flow reactor was set to 200-210° C. The plug flow feeding point was fed with the solution prepared above at a flow rate of 180 ml/min at 200-210° C. under nitrogen. The resulting reaction mass from the plug flow reactor was taken into another vessel at 20-30° C. and filtered. To the filtrate, added dichloromethane (800 ml) and slowly adjusted the pH of the reaction mixture to 1-2 using isopropanol-HCl solution. The resulting reaction mixture was stirred for about 2-4 hours for complete precipitation. The solid obtained was filtered and dried to obtain histamine dihydrochloride.

Yield: 70%

Example 3: Purification of Histamine Dihydrochloride

To histamine hydrochloride (100 g), added methanol (1000 ml) and raised the temperature of the reaction mass to 60-70° C. and stirred to get a clear solution. To the clear solution added carbon (5 g) at 50-55° C. and stirred for another 30 minutes. The solution was filtered and the solvent was partially distilled out. The resulting reaction mass was cooled slowly to 0-5° C. and stirred. The solid so obtained was filtered and dried to obtain histamine dihydrochloride having the following yield and assay.

Yield: 75%
Assay: 99.3%

The invention claimed is:

1. A process for the preparation of histamine or pharmaceutically acceptable salts thereof, comprising
    (a) preparing a solution of L-histidine of Formula II and a catalyst in a solvent;

II (b) performing a decarboxylation reaction by feeding the solution of step (a) to a continuous reactor to obtain histamine; and
    optionally converting histamine to its pharmaceutically acceptable salts.

2. The process according to claim 1, wherein the catalyst used in step (a) is selected from the group comprising of acetophenone, 4-methylacetophenone, 4-nitroacetophenone, 4-bromoacetophenone, benzoyl peroxide, 2,2'-azobisisobutyronitrile and cyclohexanone.

3. The process according to claim 1, wherein the solvent used in step (a) is selected from the group comprising of alcohols, aromatic hydrocarbon, aprotic polar solvent, water and mixtures thereof.

4. The process according to claim 1, wherein the continuous reactor is a plug flow reactor.

5. The process according to claim 1, wherein the continuous reaction has a residence time of about 30 seconds to about 10 minutes.

6. The process according to claim 1, wherein the pharmaceutically acceptable salt of histamine formed is dihydrochloride.

7. The process according to claim 1, wherein the histamine dihydrochloride is prepared with a purity of not less than 99.9%.

8. The process according to claim 1, wherein the particle size distribution of L-histidine used to prepare the solution of step (a) has a $d_{90}$ of less than 300μ.

9. The process according to claim 1, wherein the particle size distribution of L-histidine used to prepare the solution of step (a) has a $d_{90}$ value of between about 50μ and about 300μ.

10. A process for the preparation of histamine or pharmaceutically acceptable salts thereof, comprising:
    (a) preparing a solution of L-histidine of Formula II and a catalyst in a solvent;

II (b) performing a decarboxylation reaction by feeding the solution of step (a) to a continuous reactor to obtain histamine; and
    (c) optionally converting the histamine to its pharmaceutically acceptable salts,
    wherein the particle size distribution of L-histidine used to prepare the solution of step (a) has a $d_{90}$ of less than 300μ.

11. The process according to claim 10, wherein the particle size distribution of L-histidine has a $d_{90}$ less than 200μ.

12. The process according to claim 10, wherein the particle size distribution of L-histidine has a $d_{90}$ less than 100μ.

13. The process according to claim 10, wherein the particle size distribution of L-histidine has a $d_{90}$ less than 50μ.

14. The process according to claim 10, wherein the catalyst used in step (a) is selected from the group comprising of acetophenone, 4-methylacetophenone, 4-nitroacetophenone, 4-bromoacetophenone, benzoyl peroxide, 2,2′-azobisisobutyronitrile and cyclohexanone.

15. The process according to claim 10, wherein the solvent used in step (a) is selected from the group comprising of alcohols, aromatic hydrocarbon, ethers, esters, halogenated hydrocarbons, ketones, nitriles, aprotic polar solvent, water and mixtures thereof.

16. The process according to claim 10, wherein the continuous reactor used is a plug flow reactor.

17. The process according to claim 10, wherein the continuous reaction has a residence time of about 30 seconds to about 10 minutes.

18. The process according to claim 10, wherein the pharmaceutically acceptable salt of histamine formed is dihydrochloride.

19. The process according to claim 10, wherein the histamine dihydrochloride is prepared with a purity of not less than 99.9%.

20. The process according to claim 10, wherein the histamine dihydrochloride is prepared with a purity of not less than 99.3%.

* * * * *